US005759526A

United States Patent [19]

Simonnet et al.

[11] Patent Number: 5,759,526
[45] Date of Patent: Jun. 2, 1998

[54] COMPOSITION COMPRISING AN AQUEOUS DISPERSION OF LIPID VESICLES ENCAPSULATING A UV SCREENING AGENT WITH ACIDIC FUNCTIONALITY, AND USESS IN TOPICAL APPLICATION

[75] Inventors: Jean-Thierry Simonnet, Paris; Sylvie Legret, Chatillon; Alain Ribier, deceased, late of Paris; Roger Ribier, executor, Fresnes, all of France

[73] Assignee: L'Oreal, Paris, France

[21] Appl. No.: 755,314

[22] Filed: Nov. 22, 1996

[30] Foreign Application Priority Data

Nov. 22, 1995 [FR] France ................ 95 13876

[51] Int. Cl.⁶ ................ A61K 7/42; A61K 7/44; A61K 7/00
[52] U.S. Cl. ................ 424/59; 424/60; 424/400; 424/401; 424/450; 424/451
[58] Field of Search ................ 424/59, 60, 400, 424/401, 450, 451

[56] References Cited

U.S. PATENT DOCUMENTS

| 4,165,336 | 8/1979 | Bouillon et al. ................ 424/89 |
| 4,217,344 | 8/1980 | Vanlerberghe et al. ................ 424/60 |

FOREIGN PATENT DOCUMENTS

| A-0390682 | 10/1990 | European Pat. Off. . |
| A-0599502 | 9/1993 | European Pat. Off. . |
| A-0582503 | 2/1994 | European Pat. Off. . |
| A-2408387 | 6/1979 | France . |
| 2407733 | 8/1974 | Germany . |
| A-2025957 | 1/1980 | United Kingdom . |
| A-2121801 | 1/1984 | United Kingdom . |
| A2185019 | 7/1987 | United Kingdom . |

OTHER PUBLICATIONS

English Language Derwent Abstract of EP-A-559502 no date.
English Language Derwent Abstract of EP-390682 no date.
English Language Derwent Abstract of EP-582503 no date.

Primary Examiner—Shelley A. Dodson
Attorney, Agent, or Firm—Finnegan, Henderson, Farabow, Garrett & Dunner, L.L.P.

[57] ABSTRACT

A composition comprising an aqueous dispersion of lipid vesicles encapsulating at least one compound which screens out UV radiation and contains at least one free or at least partially neutralized acidic function, wherein the lipid vesicles have a lipid membrane formed from at least one nonionic amphiphilic lipid (A) or from at least one saturated hydrocarbon ionic amphiphilic lipid (B) having an iodine number of less than 10, and from at least one totally neutralized ionic amphiphilic lipid (C) is disclosed. The use of this composition as a base for products to care for the skin, the scalp, the hair, the eyelashes or the eyebrows, as a base for make-up products, and more particularly as bases for compositions to protect the human epidermis, the hair, the eyelashes or the eyebrows against ultraviolet rays are also disclosed.

59 Claims, No Drawings

COMPOSITION COMPRISING AN AQUEOUS DISPERSION OF LIPID VESICLES ENCAPSULATING A UV SCREENING AGENT WITH ACIDIC FUNCTIONALITY, AND USESS IN TOPICAL APPLICATION

The present invention relates to a composition comprising an aqueous dispersion of lipid vesicles encapsulating at least one agent for screening UV radiation, which agent contains at least one acidic function. The present invention also relates to the use of this composition in topical applications. In particular, the invention relates to the use of the composition in cosmetic or dermatological formulations for protecting the skin, the scalp, the hair, the eyelashes or the eyebrows against UV rays.

It is known that light radiation with wavelengths between 280 nm and 400 nm permits tanning of the human epidermis, and that light rays with wavelengths between 280 and 320 nm, known as UV-B rays, cause skin to burn and erythema, which may be harmful to the development of a natural tan; this UV-B radiation should thus be screened out.

It is also known that UV-A rays, with wavelengths of between 320 and 400 nm, which cause tanning of the skin, are capable of inducing an adverse change in the skin, especially in the case of sensitive skin or of skin which is continually exposed to solar radiation. UV-A rays cause, in particular, a loss of elasticity of the skin and the appearance of wrinkles, leading to premature ageing. They promote triggering of the erythemal reaction or amplify this reaction in certain individuals and may even be the cause of phototoxic or photoallergic reactions. It is thus desirable also to screen out UV-A radiation.

Many compounds intended for the photoprotection (UV-A and/or UV-B) of the skin have been proposed to date.

Compositions based on active compounds containing a free or at least partially neutralized acidic function, which screen out UV rays, are known in the state of the art. In particular, certain sulphonic compounds are known for their good properties of screening light radiation having wavelengths of between 280 and 400 nm and more particularly of between 280 and 360 nm, their heat-stability and their photochemical stability.

To improve the comfort of using these active agents with acidic functionality (softness, emollience, ease of application) and to potentiate their screening effect when compared with standard pharmaceutical forms containing them, it has been proposed to incorporate them into certain types of lipid vesicle systems. In particular, it has been proposed to incorporate the active agents into lipid vesicle systems that consist of natural ionic amphiphilic lipids whose hydrocarbon chain is unsaturated, such as soya lecithin or sunflower lecithin or into vesicle systems containing nonionic amphiphilic lipids and acidic ionic amphiphilic lipids, such as the system polyglyceryl lauryl ether/dimyristyl phosphate or the system polyglyceryl hexadecyl ether/diacetyl phosphate.

Vesicle systems containing natural ionic amphiphilic lipids whose hydrocarbon chain is unsaturated have a degree of encapsulation which is much too low to incorporate a sufficiently effective amount of screening agents with acidic functionality.

Vesicle systems containing nonionic amphiphilic lipids and acidic ionic amphiphilic lipids encapsulating a screening agent with acidic functionality have the drawback of leading instantaneously to considerable losses in the ability of the active agent to screen out UV radiation (up to 50%).

The present invention thus proposes to use a stable lipid vesicle system that makes it possible to encapsulate at least one active compound that screens out UV rays and contains at least one free or at least partially neutralized acidic function, in a sufficiently effective amount, in a long-lasting manner and without reducing the screening ability of the active agent thus encapsulated.

The inventors have discovered, unexpectedly, that encapsulation of active compounds, which screen out UV rays and contain at least one free or at least partially neutralized acidic function, with lipid vesicles whose lipid membrane is formed from at least one nonionic amphiphilic lipid or from at least one saturated hydrocarbon ionic amphiphilic lipid whose iodine number is less than 10, and from at least one totally neutralized ionic amphiphilic lipid, enables the technical problems mentioned above to be overcome and enables the objectives proposed above to be achieved.

The lipid vesicles according to the invention, which encapsulate active compounds that screen out UV rays and contain an acidic function, also make it possible to improve the distribution of these active agents on the surface of the keratin substances to be treated, to improve their persistence and their remanence and to enhance their screening effect when compared with standard pharmaceutical forms containing them.

For purposes of the present invention, remanence is understood to refer to the stability over time of the protection factor in the UV-A and/or UV-B range of an anti-sun composition subjected, after application to the skin or hair, to contact with water. The anti-sun protection associated with a given composition is characterized by assigning it a protection factor (PF) which is expressed mathematically by the ratio of the irradiation time needed to reach the erythema-forming threshold with the UV screening agent to the time needed to reach the erythema-forming threshold without a UV screening agent.

The subject of the invention is thus a composition comprising an aqueous dispersion of lipid vesicles encapsulating a compound, which compound is capable of screening out UV radiation and contains at least one free or at least partially neutralized acidic function, characterized in that the lipid vesicles have a lipid membrane formed from at least one nonionic amphiphilic lipid (A) or from at least one saturated hydrocarbon ionic amphiphilic lipid (B) having an iodine number of less than 10, and from at least one totally neutralized ionic amphiphilic lipid (C).

The compositions in accordance with the invention are more particularly oil-in-water dispersions in which the lipid vesicles act as agents for dispersing the oil in the continuous aqueous phase of the dispersion.

The lipid vesicles in accordance with the invention are more particularly vesicles with an aqueous core, i.e., encapsulating an aqueous phase.

The expression lipid vesicles with an aqueous core is understood to refer to particles formed of a membrane containing one or more concentric leaflets, these leaflets containing one or more bimolecular layers of amphiphilic lipids encapsulating an aqueous phase. The aqueous phase may contain water-soluble active substances and the bimolecular layers of amphiphilic lipids may contain lipophilic active substances.

The abovementioned vesicles with an aqueous core may be prepared by many processes. According to a first process which is described, for example, by Bangham et al. (J. Mol. Bio., 13, 1965—pages 238 to 262), the disclosure of which is incorporated herein by reference, the lipid phase is dissolved on the walls of a flask by evaporation of the solvent, the phase to be encapsulated is introduced onto the lipid film and the mixture is stirred mechanically until the dispersion of vesicles with the desired size is obtained. A dispersion of vesicles encapsulating an aqueous phase is thus obtained, the encapsulated aqueous phase and the dispersing aqueous phase being identical. According to a second, so-called "lipid co-fusion" process which is described, for example, in FR-A-2,315,991, the disclosure of which is incorporated herein by reference, the lipid phase is prepared by mixing the amphiphilic lipid(s) and the possible additives, at a temperature at which the mixture is molten, if the mixture is not liquid at room temperature. A lamellar phase is formed by introduction of the aqueous phase to be encapsulated. Next, the lamellar phase is dispersed in the form of vesicles, using an ultra-disperser, a homogenizer or ultrasound, in an aqueous dispersing phase. In a variant of this process, formation of the lamellar phase does not constitute a separate stage of the process. The vesicles obtained by these two processes are generally of "multi-leaflet" type. To obtain vesicles of "mono-leaflet" type, the teaching of FR-A-2,543, 018, the disclosure of which is incorporated herein by reference, may be used.

The nonionic amphiphilic lipids (A) forming the membrane of the vesicles of the invention are preferably chosen from the group formed from:

(i) esters and/or ethers of polyol and of fatty acid, which may or may not be polyoxyethylenated;

(ii) α-butylglycoside esters and/or ethers of fatty acid.

The esters or ethers of polyol and of fatty acid are preferably chosen from mixtures of esters or mixtures of ethers of at least one polyol chosen from the group formed by polyethylene glycol containing from 1 to 60 units of ethylene oxide, sorbitan, sorbitan containing from 2 to 60 units of ethylene oxide, glycerol containing from 2 to 30 units of ethylene oxide, polyglycerols containing from 2 to 15 units of glycerol, sucroses, glucoses containing 2 to 30 units of ethylene oxide, and at least one fatty acid containing a saturated or unsaturated, linear or branched $C_5$–$C_{22}$ alkyl chain, the number of alkyl chains per polyol group ranging from 1 to 10.

The esters of polyol and of $C_5$–$C_{22}$ fatty acids which are particularly preferred are those corresponding to the formula:

$$RCO + OCH_2 - CHOH - CH_2 +_n OH$$

where n is a value that is greater than or equal to "1" and which may contain various proportions of esters for which n=1, n=2, n=3, n=4, etc. This is also the case for esters containing several alkyl chains in their lipophilic part, such as cocoates, which contain $C_5$–$C_{22}$ alkyl chains, or isostearates in which the alkyl chains are $C_{17}$ and are a complex mixture of isomeric forms. This is also the case for products consisting of mixtures of mono-, di-, tri- or polyesters of the same polyol.

Among the commercial products which can be used according to the invention and which have the structure of a mixture of esters of polyol and of $C_5$–$C_{22}$ fatty acid as defined above, mention may preferably be made of:

the partial esters of sorbitan (or sorbitol anhydride) and of fatty acid, sold under the trade names "Span 20, 40, 60 and 80" by the company "ICI";

sorbitan isostearate, sold under the trade name "Si 10 R Nikkol" by the company "Nikko";

sorbitan stearate containing 4 units of ethylene oxide, sold under the trade name "Tween 61" by the company "ICI";

polyethylene glycol stearate containing 8 units of ethylene oxide, sold under the name "MYR J 45" by "ICI";

polyethylene glycol monostearate of formula

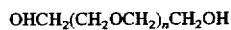

in which formula n is equal to 4, sold under the name "MYS 4" by the company "Nikko";

polyethylene glycol stearate of molecular weight 400, of chemical grade or of biotechnological grade, sold by the company "Unichema";

diglyceryl stearate containing 4 units of ethylene oxide, sold under the name "Hostacerine DGS" by the company "Hoechst";

tetraglyceryl stearate, sold under the name "Tetraglyn 1S" by the company "Nikko";

diglyceryl isostearate, sold by the company "Solvay";

diglyceryl distearate, sold under the name "Emalex DSG 2" by the company "Nihon";

sucrose mono-, di- and tripalmitostearate, sold under the names "F50, F70, F110 and F160 Crodesta" by the company "Croda";

the mixture of sucrose mono- and dipalmitostearate, sold under the name "Grilloten PSE 141 G" by the company "Grillo";

the mixture of sucrose stearate and sucrose cocoate, sold under the name "Arlatone 2121" by the company "ICI"; and methyl glucose distearate containing 20 units of ethylene oxide, sold under the name "Glucam E20 distearate" by the company "Amerchol".

The α-butylglucoside esters and ethers of fatty acid used according to the invention are preferably either mixtures of α-butylglucoside esters and/or mixtures of α-butylglucoside ethers of different fatty acids in which the various fatty chains contain, relative to each other, a similar number of carbon atoms, for example differing by one or two, or mixtures of α-butylglucoside mono-, di-, tri- or polyesters and/or mixtures of α-butylglucoside mono-, di-, tri- or polyethers of the same fatty acid.

The α-butylglucoside esters and ethers of fatty acid used according to the invention preferably contain a fatty chain having from 8 to 24 carbon atoms, more preferably from 12 to 22 carbon atoms and still more preferably, from 14 to 18 carbon atoms.

The α-butylglucoside esters and ethers of lauric acid ($C_{12}$), of myristic acid ($C_{14}$), of palmitic acid ($C_{16}$), of stearic acid ($C_{18}$) and of behenic acid ($C_{22}$) may be preferably mentioned.

A mixture of palmitic acid mono- and diester of α-butylglucoside obtained according to the enzymatic manufacturing process described for the lipid vesicles in accordance with the invention is used more particularly.

The α-butylglucoside esters and ethers of fatty acid in accordance with the invention may be prepared from α-butylglucoside obtained according to the enzymatic manufacturing process described in French patent application FR-A-2,680,373, which consists in placing butanol in contact with starch, maltodextrins or maltose in the presence of a purified enzymatic preparation which has a-transglucosylation activity. The α-butylglucoside esters and ethers of fatty acid may be synthesized by reacting the corresponding fatty acid or fatty acid mixture with α-butylglucoside according to standard processes.

The saturated hydrocarbon ionic amphiphilic lipids (B) having an iodine number less than 10, and forming the membrane of the vesicles of the invention are preferably chosen from synthetic phospholipids such as dipalmitoylphosphatidylcholine or phospholipids modified chemically or enzymatically, such as hydrogenated lecithin.

The totally neutralized ionic amphiphilic lipids (C) are preferably chosen from those having totally neutralized acidic functions, and more particularly from the group:
(i) disodium or dipotassium acylglutamates;
(ii) alkali metal salts of dicetyl phosphate and of dimyristyl phosphate, in particular the Na and K salts;
(iii) phospholipids;
(iv) alkylsulphonic derivatives of formula:

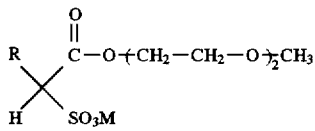

in which formula R represents $C_{12}$–$C_{22}$ radicals, in particular $C_{16}H_{33}$ and $C_{18}H_{37}$ radicals, taken as a mixture or separately, and M is an alkali metal, preferably sodium;
(v) salicylic acid derivatives as described and prepared in European patent application EP-A-585,170 of formula (1):

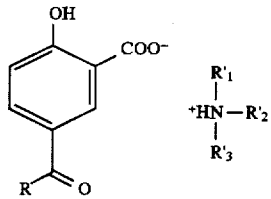

in which R represents a linear or branched $C_{11}$–$C_{17}$ alkyl radical; $R'_1$, $R'_2$ and $R'_3$, which may be identical or different, represent a $C_1$–$C_{18}$ alkyl or hydroxyalkyl radical, it being possible for one of the radicals $R'_1$, $R'_2$ and $R'_3$ to be a benzyl radical;
(vi) alkali metal salts of cholesteryl sulphate, in particular the Na salt;
(vii) alkali metal salts of cholesteryl phosphate, in particular the Na salt; and
(viii) alkali metal salts of phosphatidic acid, in particular the Na salt.

The totally neutralized ionic amphiphilic lipids (C) which are particularly preferred are chosen from the group consisting of disodium acylglutamates such as the disodium salt of N-stearoylglutamic acid marketed under the name "Acylglutamate HS 21" by the company Ajinomoto and salicylic derivatives of formula (1), such as, N,N-dimethyl-N-(2-hydroxyethyl)ammonium 5-n-dodecanoylsalicylate.

According to a preferred embodiment of the invention, the weight ratio between the amount of nonionic amphiphilic lipid (A) or of saturated hydrocarbon ionic amphiphilic lipid (B) and the amount of totally neutralized ionic amphiphilic lipid (C) ranges from 50/1 to 50/25, and the weight ratio between the amount of lipid phase and the amount of aqueous phase in the dispersion ranges from 1/1000 to 300/1000.

In the composition according to the invention, the vesicles with an aqueous core preferably have an average diameter ranging from 10 to 5000 nm.

The vesicles of the compositions according to the invention may additionally contain one or more active compound (s) having a cosmetic and/or dermopharmaceutical activity, which compounds, depending on their solubility characteristics, may have different localizations. If the active agents are water-soluble, they are preferably introduced into the encapsulated aqueous phase of the vesicles with an aqueous core. If the active agents are liposoluble, they are preferably introduced into the lipid phase which forms the membrane.

If the active agents are amphiphilic, they distribute themselves between the lipid phase and the encapsulated aqueous phase of the vesicles with an aqueous core, with a partition coefficient which varies according to the nature of the amphiphilic active agent.

It is possible, in a known manner, to incorporate at least one additive into the lipid phase which forms the lipid membrane of the vesicles with an aqueous core of the invention, the main function of this additive being to decrease the permeability of the vesicles, to prevent their flocculation and their fusion or to increase the degree of encapsulation.

According to another preferred embodiment of the invention, at least one additive may be added to the lipid phase, this additive preferably being chosen from the group formed by:

sterols, and in particular phytosterols and cholesterol, long-chain alcohols and diols, long-chain amines and their quaternary ammonium derivatives.

These additives may possibly have a cosmetic and/or dermopharmaceutical activity. This is the case, for example, for cholesterol.

The UV screening compounds which have at least one free or at least partially neutralized acidic function, according to the present invention, are preferably chosen from water-soluble screening agents having at least one sulphonic acid function, $SO_3H$.

As examples of acidic screening agents containing at least one $SO_3H$ group, mention may preferably be made of 3-benzylidene-2-bornanone sulphonic derivatives and in particular those of formulae (I), (II), (III), (IV) and (V) below:

Formula (I):

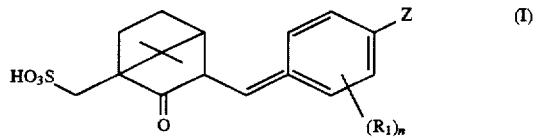

in which:

Z represents a group

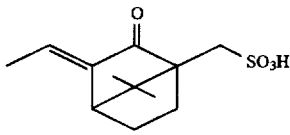

n is equal to 0 or is an integer ranging from 1 to 4 ($0 \leq n \leq 4$)

$R_1$ represents one or more linear or branched alkyl or alkoxy radicals, which may be identical or different, containing from 1 to 4 carbon atoms approximately.

A particularly preferred compound of formula I is that corresponding to n=0: benzene-1,4-[di(3-methylidene-10-camphorsulphonic)] acid.

Formula (II):

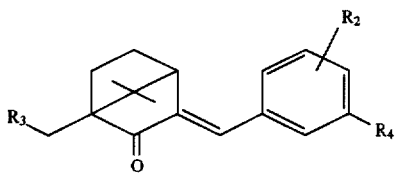

in which:
- R₂ represents a hydrogen atom, a halogen atom, an alkyl radical containing from 1 to 4 carbon atoms approximately or an —SO₃H radical;
- R₃ and R₄ represent a hydrogen atom or an —SO₃H radical, at least one of the radicals R₂, R₃ or R₄ representing the —SO₃H radical, R₂ and R₄ not being able simultaneously to represent an —SO₃H radical.

Specific examples which may be mentioned are the following compounds of formula II in which:

- R₂ represents the —SO₃H radical in the para position of benzylidenecamphor and R₃ and R₄ each represent a hydrogen atom, that is to say 4-(3-methylidenecamphor)benzenesulphonic acid.
- R₂ and R₄ each represent a hydrogen atom and R₃ represents an —SO₃H radical, that is to say 3-benzylidene-10-camphorsulphonic acid.
- R₂ represents a methyl radical in the para position of benzylidenecamphor, R₄ represents an —SO₃H radical and R₃ represents a hydrogen atom, that is to say 2-methyl-5-(3-methylidenecamphor)benzenesulphonic acid.
- R₂ represents a chlorine atom in the para position of benzylidenecamphor, R₄ represents an —SO₃H radical and R₃ represents a hydrogen atom, that is to say 2-chloro-5-(3-methylidenecamphor)benzenesulphonic acid.
- R₂ represents a methyl radical in the para position of benzylidenecamphor, R₄ represents a hydrogen atom and R₃ represents an —SO₃H radical, that is to say 3-(4-methyl)benzylidene-10-camphorsulphonic acid.

Formula (III):

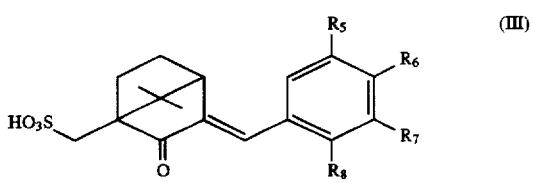

in which:
- R₅ and R₇ represent a hydrogen atom, a hydroxyl radical or a linear or branched alkyl or alkoxy radical containing from 1 to 8 carbon atoms approximately, at least one of the radicals R₅ and R₇ representing a hydroxyl, alkyl or alkoxy radical,
- R₆ and R₈ represent a hydrogen atom or a hydroxyl radical, at least one of the radicals R₆ and R₈ representing a hydroxyl radical, with the proviso that when R₅ and R₈ represent a hydrogen atom and when R₆ represents a hydroxyl radical, R₇ cannot represent an alkoxy radical or a hydrogen atom.

Specific examples which may be mentioned are the following compounds of formula (III) in which:

- R₅ is a methyl radical, R₆ is a hydrogen atom, R₇ is a tert-butyl radical and R₈ is a hydroxyl radical, that is to say (3-t-butyl- 2-hydroxy-5-methyl)benzylidene-10-camphorsulphonic acid.
- R₅ is a methoxy radical, R₆ is a hydrogen atom, R₇ is a tert-butyl radical and R₈ is a hydroxyl radical, that is to say (3-t-butyl-2-hydroxy-5-methoxy)benzylidene-10-camphorsulphonic acid.
- R₅ and R₇ each represent a tert-butyl radical, R₆ represents a hydroxyl radical and R₈ represents a hydrogen atom, that is to say (3,5-di-tert-butyl-4-hydroxy)benzylidene-10-camphorsulphonic acid.

Formula (IV):

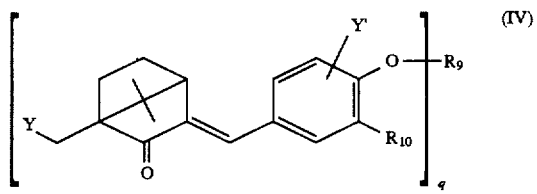

in which:
- represents a hydrogen atom, a linear or branched alkyl radical containing from 1 to 18 carbon atoms approximately, a linear or branched alkenyl radical containing from 3 to 18 carbon atoms approximately, a group selected from:

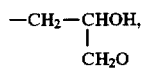

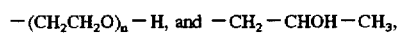

or alternatively a divalent radical: —(CH₂)ₘ— or —CH₂—CHOH—CH₂— n being an integer ranging from 1 to 6 (1≦n≦6) and m being an integer ranging from 1 to 10 (1≦m≦10),

- R₁₀ represents a hydrogen atom, an alkoxy radical containing from 1 to 4 carbon atoms approximately or a divalent radical —O— connected to the radical R₉ when the latter is also divalent,
- q represents an integer equal to 1 or 2, it being understood that if q is equal to 2, R₉ must represent a divalent radical,
- Y and Y' represent a hydrogen atom or an —SO₃H radical, at least one of these radicals Y or Y' being other than hydrogen.

Specific examples which may be mentioned are the following compounds of formula (IV) in which:

- q is equal to 1, Y and R₁₀ each represent a hydrogen atom, R₉ represents a methyl radical and Y' in position 3 represents an —SO₃H radical, that is to say 2-methoxy-5-(3-methylidenecamphor)benzenesulphonic acid;
- q is equal to 1, Y represents an —SO₃H radical, Y' represents a hydrogen atom and R₁₀ represents a divalent radical —O— connected to R₉ representing a methylene radical, that is to say 3-(4,5-methylenedioxy)benzylidene-10-camphorsulphonic acid;
- q is equal to 1, Y represents an —SO₃H radical, Y' and R₁₀ both represent a hydrogen atom and R₉ represents a methyl radical, that is to say 3-(4-methoxy)benzylidene-10-camphorsulphonic acid;
- q is equal to 1, Y represents an —SO₃H radical, Y' represents a hydrogen atom, R₉ represents a methyl radical and R₁₀ represents a methoxy radical, that is to say 3-(4,5-dimethoxy)benzylidene-10-camphorsulphonic acid;
- q is equal to 1, Y represents an —SO₃H radical, Y' and R₁₀ both represent a hydrogen atom and R₉ represents an n-butyl radical, that is to say 3-(4-n-butoxy) benzylidene-10-camphorsulphonic acid; and q is equal to 1, Y represents an —SO$_3$H radical, Y' represents a hydrogen atom, R$_9$ represents an n-butyl radical and R$_{10}$ represents a methoxy radical, that is to say 3-(4-n-butoxy-5-methoxy)benzylidene-10-camphorsulphonic acid.

Formula (V):

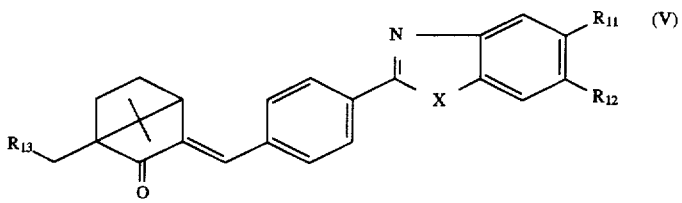

in which:

R$_{11}$ represents a hydrogen atom, a linear or branched alkyl or alkoxy radical containing from 1 to 6 carbon atoms approximately or an —SO$_3$H radical, R$_{12}$ represents a hydrogen atom or a linear or branched alkyl or alkoxy radical containing from 1 to 6 carbon atoms approximately, R$_{13}$ represents a hydrogen atom or an —SO$_3$H radical, at least one of the radicals R$_{11}$ and R$_{13}$ representing an —SO$_3$H radical.

X is an oxygen or sulphur atom or a group —NR—, R being a hydrogen atom or a linear or branched alkyl radical containing from 1 to 6 carbon atoms approximately.

A specific example of a compound of formula (V) which may be mentioned is the compound in which X represents an —NH— radical, R$_{11}$ represents an —SO$_3$H radical and R$_{12}$ and R$_{13}$ both represent a hydrogen atom, that is to say 2-[4-(camphormethylidene)phenyl]benzimidazole-5-sulphonic acid.

The compounds of structures (I), (II), (III), (IV) and (V) are respectively described in U.S. Pat. No. 4,585,597 and French patent Nos. FR 2,236,515, FR 2,282,426, FR 2,645,148, FR 2,430,938 and FR 2,592,380, the disclosure of each of which is incorporated herein by reference.

The screening agent with a sulphonic group may also be a benzophenone sulphonic derivative of formula (VI):

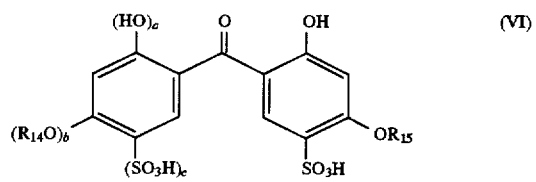

in which:

R$_{14}$ and R$_{15}$, which may be identical or different, represent either a hydrogen atom or a linear or branched alkyl radical containing from 1 to 8 carbon atoms approximately;

a, b and c, which may be identical or different, are equal to 0 or 1.

A specific example of a compound of formula (VI) which may be mentioned is 2-hydroxy-4-methoxybenzophenone-5-sulphonic acid, i.e., a compound of formula VI in which a, b and c are equal to 0 and R$_{15}$ represents a methyl radical.

The screening agent with a sulphonic group may also be a benzimidazole sulphonic derivative of formula:

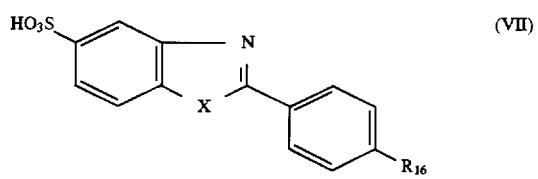

in which:

X represents an oxygen atom or an —NH— radical

R$_{16}$ represents a hydrogen atom, a linear or branched alkyl or alkoxy radical containing from 1 to 8 carbon atoms approximately or a group of formula

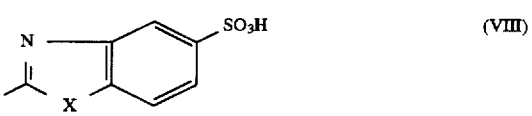

in which X' represents an oxygen atom or an —NH— radical.

Specific examples which may be mentioned are the following compounds of formula (VII) in which:

X represents the —NH— radical and R$_{16}$ represents a hydrogen atom: 2-phenylbenzimidazole-5-sulphonic acid;

X represents the —NH— radical and R$_{16}$ represents the group of formula (VIII) in which X' represents the —NH— radical:benzene-1,4-di(benzimidazol-2-yl-5-sulphonic) acid;

X represents an oxygen atom and R$_{16}$ represents the group of formula (VIII) in which X' represents an oxygen atom:benzene-1,4-di(benzoxazol-2-yl-5-sulphonic) acid.

The compounds of formula VI and VII are known compounds which may be prepared according to standard methods described in the prior art.

The screening compounds with acidic functionality are present in the compositions of the invention in concentrations preferably ranging from 0.1 to 10% by weight of active substance relative to the total weight of the composition, and more particularly from 0.5 to 5% by weight of active substance.

The continuous aqueous phase of the composition in accordance with the invention preferably contains an oil dispersed in the latter by lipid vesicles.

The oil may be chosen in particular from the group formed by:

animal or plant oils formed by fatty acid esters of polyols, in particular liquid triglycerides, for example sunflower oil, corn oil, soya oil, marrow oil, grapeseed oil, jojoba oil, sesame oil, hazelnut oil, fish oils, glyceryl tricaprocaprylate, or the plant or animal oils thereof of formula R$_9$COOR$_{10}$, in which formula R$_9$ represents a higher fatty acid residue containing from 7 to 19 carbon atoms and R$_{10}$ represents a branched hydrocarbon chain containing from 3 to 20 carbon atoms, for example purcellin oil;

natural or synthetic essential oils such as, for example, eucalyptus oil, hybrid lavender oil, lavender oil, vetiver oil, Litsea cubeba oil, lemon oil, sandlewood oil, rosemary oil, camomile oil, savory oil, nutmeg oil, cinnamon oil, hyssop oil, caraway oil, orange oil, geraniol oil, cade oil and bergamot oil;

hydrocarbons such as hexadecane and liquid paraffin;

halogenated carbons, in particular fluorocarbons such as fluoroamines, for example perfluorotributylamine, fluorohydrocarbons, for example perfluorodecahydronaphthalene, fluoro esters and fluoro ethers;

silicones, for example polysiloxanes, polydimethylsiloxanes and fluorosilicones;

esters of inorganic acid and of an alcohol; and ethers and polyethers.

The continuous aqueous phase of the composition according to the invention may also contain water-soluble cosmetic and/or dermopharmaceutical active agents. The oil dispersed by the lipid vesicles may optionally contain a liposoluble active agent.

The continuous aqueous dispersing phase may also contain adjuvants which have no intrinsic cosmetic or dermopharmaceutical activity but which are used to formulate the dispersion in the form of a lotion, a cream, a milk or a serum. These adjuvants are taken in particular from the group formed by gelling agents, preserving agents, dyes, opacifiers and fragrances. Among the gelling agents which can be used, mention may be made of alga derivatives such as satiagum, natural gums such as tragacanth, and synthetic polymers, in particular the polycarboxyvinylic acid mixtures marketed under the name "Hostacerin PN 73" by the company "Hoechst" or under the name "Carbopol" by "Goodrich".

Another subject of the invention includes compositions for topical use. They are characterized in that they contain the compositions as defined above.

Another subject of the invention includes the use of the compositions as defined above to care for at least one of the skin, the scalp, the hair, the eyelashes, and the eyebrows as a base for make-up products.

Another subject of the invention includes the use of the compositions as defined above as a base for make-up products.

The cosmetic or dermopharmaceutical products obtained from the compositions of the invention may be in the form of a relatively thickened oil-in-water dispersion, a gel, a cream, a milk or a serum.

The cosmetic compositions of the invention may be used as compositions for protecting the human epidermis, the hair, the eyelashes or the eyebrows against ultraviolet rays, as an anti-sun product or as a make-up product.

When the cosmetic compositions according to the invention are used to protect the hair and the scalp, they may be in the form of a shampoo, a lotion or a gel and may constitute, for example, a rinse-out composition, to be applied before or after shampooing, before or after dyeing or bleaching or before, during or after permanent-waving or straightening of the hair, a styling or treating lotion or gel, a blow-drying or hair-setting lotion or gel, or a composition for permanent-waving, straightening, dyeing or bleaching the hair.

When the cosmetic or dermatological compositions are used to protect the skin, the eyelashes or the eyebrows, they may be in the form of a cream for treating the epidermis, a foundation, a mascara or an eyeliner.

Another subject of the present invention is a method for the non-therapeutic treatment of the skin, the scalp, the hair, the eyelashes or the eyebrows which is intended to protect them against the effects of UV rays, this process comprising applying to the latter an effective amount of a cosmetic composition as defined above.

The examples below, which are given purely by way of illustration and with no limitation being implied, will allow a better understanding of the invention to be gained.

In all the examples given below, the vesicle dispersions were prepared by the so-called "lipid co-fusion" process, in which:

in a first step, the lipid phase was prepared by mixing together, in liquid form, various amphiphilic lipids of which it was composed, optionally combined with liposoluble active agents or additives, and the lipid phase obtained was placed in the presence of an aqueous phase optionally containing water-soluble active agents, so as to obtain a lamellar phase;

in a second step, an aqueous dispersing phase optionally containing an oil and various additives was added to the hydrated lamellar phase obtained; and in a third step, the mixture was subjected to vigorous stirring in a homogenizer in order to obtain vesicles dispersed in an aqueous dispersing phase.

EXAMPLE 1

Facial serum

| First phase: | |
| --- | --- |
| - Polyethylene glycol stearate of molecular weight 400 (A), produced biotechnologically, sold by the company "Unichema" | 0.95% |
| - Cholesterol | 0.95% |
| - Disodium salt of N-stearoylglutamic acid (C) marketed under the name "Acylglutamate HS 21" by the company Ajinomoto | 0.1% |
| - Benzene-1,4-[di(3-methylidene-10-camphorsulphonic)] acid (acidic UV screening agent) | 2.0% |
| - Triethanolamine to neutralize the acidic UV screening agent | 0.4% |
| - Glycerol | 3.00% |
| - Preserving agents | 0.3% |
| - Lactic hydrolysate marketed under the name Lactolan LS by Laboratoires Sérobiologiques, Nancy | 5.0% |
| - Aqueous solution of superoxide dismutase at 5000 U/ml, marketed by the company Pentapham | 1.0% |
| Second phase: | |
| - Polycarboxyvinylic acid mixture marketed under the name "Carbopol" (gelling agent) by the company Goodrich | 0.20% |
| - L-lysine monohydrate | qs pH 6.5 |
| - Demineralized water | qs 100% |

EXAMPLE 2

Facial cream

| First phase: | |
| --- | --- |
| - Sorbitan stearate containing 4 mol of ethylene oxide sold under the name Tween 61 by ICI (A) | 3.8% |
| - N,N-dimethyl-N-(2-hydroxyethyl)ammonium 5-dodecanoylsalicylate (C) | 0.4% |
| - Cholesterol | 3.8% |

| -continued | |
|---|---|
| - Benzene-1,4-[di(3-methylidene-10-camphorsulphonic)] acid (acidic UV screening agent) | 5.00% |
| - Triethanolamine to neutralize the acidic UV screening agent | 1.0% |
| - Tocopheryl acetate | 0.5% |
| - Glycerol | 5.0% |
| - Demineralized water | qs 50% |
| Second phase: | |
| - Macadamia oil | 20.0% |
| - Fragrance | 0.2% |
| - Polycarboxyvinylic acid mixture marketed under the name "Carbopol" (gelling agent) by the company Goodrich | 0.42% |
| - Preserving agents | 0.3% |
| - Triethanolamine | qs pH = 6 |
| - Demineralized water | qs 100% |

EXAMPLE 3

Facial day cream

| First phase: | |
|---|---|
| - Polyethylene glycol stearate of molecular weight 400 (A), produced biotechnologically, sold by the company Unichema | 0.9% |
| - N,N-dimethyl-N-(2-hydroxyethyl)ammonium 5-dodecanoylsalicylate (C) | 0.1% |
| - Benzene-1,4-[di(3-methylidene-10-camphorsulphonic)] acid (acidic UV screening agent) | 3.0% |
| - Triethanolamine to neutralize the acidic UV screening agent | 1.0% |
| - Glycerol | 3.0% |
| - Demineralized water | qs 65% |
| Second phase: | |
| - Tocopheryl acetate | 1.0% |
| - Jojoba oil | 5.0% |
| - Volatile silicone oil | 4.0% |
| - Fragrance | 0.3% |
| - Polycarboxyvinylic acid mixture marketed under the name "Carbopol" (gelling agent) by the company Goodrich | 0.1% |
| - Triethanolamine | qs pH = 6 |
| - Demineralized water | qs 100% |

EXAMPLE 4

Facial day cream

| First phase: | |
|---|---|
| - Diglyceryl distearate (A) sold under the name Emalex PSGA by the company Nihon Emulsion | 3.6% |
| - Disodium salt of N-stearoylglutamic acid (C) marketed under the name "Acylglutamate HS 21" by the company Ajinomoto | 0.8% |
| - Cholesterol | 3.6% |
| - Benzene-1,4-[di(3-methylidene-10-camphorsulphonic)] acid (acidic UV screening agent) | 7.0% |
| - Triethanolamine to neutralize the acidic UV screening agent | 1.4% |
| - Tocopheryl acetate | 0.5% |
| - Glycerol | 5.0% |
| - Demineralized water | qs 50% |

| -continued | |
|---|---|
| Second phase: | |
| - Sweet almond oil | 4.0% |
| - Grapeseed oil | 8.0% |
| - Sunflower oil | 8.0% |
| - Volatile silicone oil | 3.0% |
| - Fragrance | 0.2% |
| - Polycarboxyvinylic acid mixture marketed under the name "Carbopol" (gelling agent) by the company Goodrich | 0.42% |
| - Triethanolamine | qs pH = 6 |
| - Demineralized water | qs 100% |

What is claimed is:

1. A composition comprising an aqueous dispersion of an aqueous phase and a lipid phase, said aqueous dispersion containing lipid vesicles encapsulating a compound which screens out UV radiation, wherein said compound contains at least one free or at least partially neutralized acidic function, and wherein said lipid vesicles have a lipid membrane formed from: at least one nonionic amphiphilic lipid (A) or at least one saturated hydrocarbon ionic amphiphilic lipid (B) having an iodine number of less than 10; and at least one totally neutralized ionic amphiphilic lipid (C).

2. A composition according to claim 1, which is in the form of an oil-in-water dispersion in which said lipid vesicles act as an agent for dispersing an oil in the aqueous phase of said dispersion.

3. A composition according to claim 1, wherein said lipid vesicles are lipid vesicles with an aqueous core.

4. A composition according to claim 1, wherein said at least one nonionic amphiphilic lipid (A) forming the membrane of said lipid vesicles is selected from:

(i) esters of polyol and fatty acid, polyoxyethylenated esters of polyol and fatty acid, ethers of polyol and fatty acid, and polyethylenated ethers of polyol and fatty acid; and (ii) α-butylglycoside esters of fatty acid, and α-butylglycoside ethers of fatty acid.

5. A composition according to claim 4, wherein said at least one nonionic amphiphilic lipid (A) is a mixture of (1) at least one ester or ether of at least one polyol selected from polyethylene glycol containing from 1 to 60 units of ethylene oxide, sorbitan, sorbitan containing from 2 to 60 units of ethylene oxide, glycerol containing from 2 to 30 units of ethylene oxide, polyglycerols containing from 2 to 15 units of glycerol, sucroses, and glucoses containing from 2 to 30 units of ethylene oxide, and (2) at least one fatty acid containing a saturated or unsaturated, linear or branched $C_5$–$C_{22}$ alkyl chain, the number of alkyl chains per polyol group ranging from 1 to 10.

6. A composition according to claim 4, wherein said at least one nonionic amphiphilic lipid (A) is selected from α-butylglycoside esters of fatty acid, and α-butylglycoside ethers of fatty acid, wherein the fatty chain of said fatty acid has from 8 to 24 carbon atoms.

7. A composition according to claim 6, wherein said at least one nonionic amphiphilic lipid (A) is selected from α-butylglycoside esters of fatty acid, and α-butylglycoside ethers of fatty acid wherein the fatty chain of said fatty acid has from 12 to 22 carbon atoms.

8. A composition according to claim 7, wherein said at least one nonionic amphiphilic lipid (A) is selected from α-butylglycoside esters of fatty acid, and α-butylglycoside ethers of fatty acid wherein the fatty chain of said fatty acid has from 14 to 18 carbon atoms.

9. A composition according to claim 6, wherein said at least one nonionic amphiphilic lipid (A) is selected from α-butylglucoside esters and α-butylglucoside ethers of lauric acid ($C_{12}$), of myristic acid ($C_{14}$), of palmitic acid ($C_{16}$), of stearic acid ($C_{18}$) and of behenic acid ($C_{22}$).

10. A composition according to claim 9, wherein said at least one nonionic amphiphilic lipid (A) is a mixture of α-butylglucoside mono- and diester of palmitic acid.

11. A composition according to claim 6, wherein said at least one nonionic amphiphilic lipid (A) is selected from: (1) mixtures of α-butylglucoside esters of different fatty acids, of α-butylglucoside ethers of different fatty acids, and of at least one of said esters and at least one of said ethers, wherein the chain length of the fatty acids differ by one or two carbon atoms; and (2) mixtures of α-butylglucoside mono-, di-, tri- or polyesters of the same fatty acid, mixtures of α-butylglucoside mono-, di-, tri- or polyethers of the same fatty acid, and mixtures of at least one of said polyesters and at least one of said polyethers.

12. A composition according to claim 1, wherein said at least one saturated hydrocarbon ionic amphiphilic lipid (B) forming the membrane of said lipid vesicles is selected from synthetic phospholipids and phospholipids modified chemically or enzymatically.

13. A composition according to claim 1, wherein said at least one totally neutralized ionic amphiphilic lipid (C) forming the membrane of said lipid vesicles is selected from ionic amphiphilic lipids having totally neutralized acidic functions.

14. A composition according to claim 13, wherein said at least one totally neutralized ionic amphiphilic lipids (C) forming the membrane of said lipid vesicles is selected from:

(i) disodium and dipotassium acylglutamates;
(ii) alkali metal salts of dicetyl phosphate and of dimyristyl phosphate;
(iii) phospholipids;
(iv) alkylsulphonic derivatives of formula:

$$\underset{H}{\overset{R}{\diagdown}}\underset{SO_3M}{\overset{C-O+CH_2-CH_2-O\overline{)_{\overline{2}}}CH_3}{\diagup}}$$

wherein R represent a $C_{12}$–$C_{22}$ radical, and M is an alkali metal;

(v) salicylic acid derivatives of formula (1):

(1)

OH
COO⁻        R'₁
             |
            ⁺HN—R'₂
             |
            R'₃
R—C(=O)—O wherein R represents a linear or branched $C_{11}$–$C_{17}$ alkyl radical; R'₁, R'₂ and R'₃, which may be identical or different, represent a $C_1$–$C_{18}$ alkyl or hydroxyalkyl radical, it being possible for one of the radicals R'₁, R'₂ and R'₃ to be a benzyl radical;
(vi) alkali metal salts of cholesteryl sulphate;
(vii) alkali metal salts of cholesteryl phosphate; and
(viii) alkali metal salts of phosphatidic acid.

15. A composition according to claim 14, wherein R in said alkyl sulphonic derivatives is selected from a $C_{16}H_{33}$ radical, a $C_{18}H_{37}$ radical or a mixture thereof.

16. A composition according to claim 14, wherein said at least one totally neutralized ionic amphiphilic lipid (C) is selected from the disodium salt of N-stearoylglutamic acid and N,N-dimethyl-N-(2-hydroxyethyl)ammonium 5-n-dodecanoylsalicylate.

17. A composition according to claim 1, wherein the weight ratio between the amount of nonionic amphiphilic lipid (A) or saturated hydrocarbon ionic amphiphilic lipid (B) and the amount of totally neutralized ionic amphiphilic lipid (C) ranges from 50/1 to 50/25, and wherein the weight ratio between the amount of lipid phase and the amount of aqueous phase in the dispersion ranges from 1/1000 to 300/1000.

18. A composition according to claim 1, wherein said lipid vesicles further contain at least one water-soluble, liposoluble or amphiphilic active compound having at least one activity which is cosmetic or dermopharmaceutical.

19. A composition according to claim 1, wherein said lipid vesicles further contain at least one additive whose main function is to reduce the permeability of the vesicles, to prevent their flocculation and their fusion, or to increase the degree of encapsulation.

20. A composition according to claim 19, wherein said at least one additive is selected from:

sterols, long-chain alcohols and diols, and long-chain amines and their quaternary ammonium derivatives.

21. A composition according to claim 18, wherein said at least one active compound is cholesterol.

22. A composition according to claim 1, wherein said compound which screens out UV radiation is a water-soluble screening agent which has at least one sulphonic radical —$SO_3H$.

23. A composition according to claim 1, wherein said compound which screens out UV radiation is a 3-benzylidene-2-bornanone derivative.

24. A composition according to claim 22, wherein said compound which screens out UV radiation corresponds to formula (I):

(I)

HO₃S—[bornane]=CH—[phenyl]—Z
              O         (R₁)ₙ wherein:

—Z represents a group of formula

[vinyl]=[bornane]—CH₂—SO₃H
              O n represents 0 or is an integer ranging from 1 to 4

R₁ represents one or more linear or branched alkyl or alkoxy radicals, which may be identical or different, containing from 1 to 4 carbon atoms.

25. A composition according to claim 24, wherein said compound of formula (I) is benzene-1,4-[di(3-methylidene-10-camphorsulphonic)] acid.

26. A composition according to claim 22, wherein said compound which screens out UV radiation corresponds to formula (II):

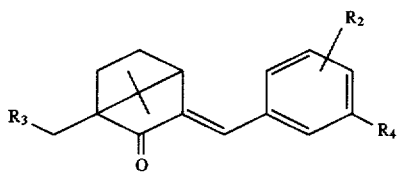

wherein
- $R_2$ represents a hydrogen atom, a halogen atom, an alkyl radical containing from 1 to 4 carbon atoms or an —$SO_3H$ radical, and
- $R_3$ and $R_4$ independently represent a hydrogen atom or an —$SO_3H$ radical, wherein at least one of the radicals $R_2$, $R_3$ or $R_4$ represents an —$SO_3H$ radical, and wherein $R_2$ and $R_4$ do not simultaneously represent an —$SO_3H$ radical.

27. A composition according to claim 26, wherein, in form (II), $R_2$ represents an —$SO_3H$ radical in the para position and $R_3$ and $R_4$ each represent a hydrogen atom.

28. A composition according to claim 26, wherein, in formula (II), $R_2$ and $R_4$ each represent a hydrogen atom and $R_3$ represents —$SO_3H$.

29. A composition according to claim 26, wherein, in formula (II), $R_2$ represents a methyl radical in the para position, $R_4$ represents an $SO_3H$ radical and $R_3$ represents a hydrogen atom.

30. A composition according to claim 26, wherein, in formula (II), $R_2$ represents a chlorine atom in the para position, $R_4$ represents an—$SO_3H$ radical and $R_3$ represents a hydrogen atom.

31. A composition according to claim 26, wherein, in formula (II), $R_2$ represents a methyl radical in the para position, $R_4$ represents a hydrogen atom and $R_3$ represents an —$SO_3H$ radical.

32. A composition according to claim 22, wherein said compound which screens out UV radiation corresponds to formula (III):

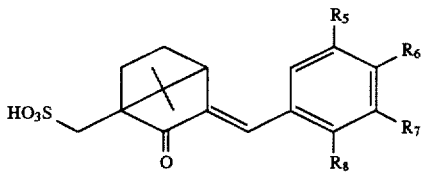

in which:
- $R_5$ and $R_7$ each independently represent a hydrogen atom, a hydroxyl radical, a linear or branched alkyl radical containing from 1 to 8 carbon atoms or a linear or branched alkoxy radical containing from 1 to 8 carbon atoms, wherein at least one of the radicals $R_5$ and $R_7$ represents a hydroxyl, alkyl or alkoxy radical,
- $R_6$ and $R_8$ each independently represent a hydrogen atom or a hydroxyl radical, wherein at least one of the radicals $R_6$ and $R_8$ represents a hydroxyl radical,
- with the proviso that when $R_5$ and $R_8$ represent a hydrogen atom and when $R_6$ represents a hydroxyl radical, $R_7$ cannot represent an alkoxy radical or a hydrogen atom.

33. A composition according to claim 32, wherein, in formula (III), $R_5$ is a methyl radical, $R_6$ is a hydrogen atom, $R_7$ is a tert-butyl radical and $R_8$ is a hydroxyl radical.

34. A composition according to claim 32, wherein, in formula (III), $R_5$ is a methoxy radical, $R_6$ is a hydrogen atom, $R_7$ is a tert-butyl radical and $R_8$ is a hydroxyl radical.

35. A composition according to claim 32, wherein, in formula (III), $R_5$ and $R_7$ each represent a tert-butyl radical, $R_6$ represents a hydroxyl radical and $R_8$ represents a hydrogen atom.

36. A composition according to claim 22, wherein said compound which screens out UV radiation corresponds to formula (IV):

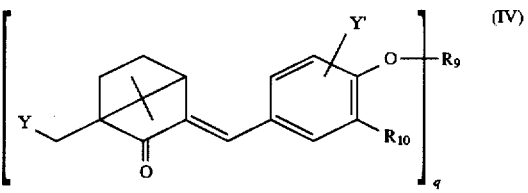

wherein:
- $R_9$ represents a hydrogen atom; a linear or branched alkyl radical containing from 1 to 18 carbon atoms; a linear or branched alkenyl radical containing from 3 to 18 carbon atoms; a group selected from:

$$-CH_2-\underset{\underset{CH_2O}{|}}{C}HOH, \quad -(CH_2CH_2O)_n-H, \text{ and}$$

$$-CH_2-CHOH-CH_3,$$

or a divalent radical selected from: —$(CH_2)_m$— and —$CH_2$—$CHOH$—$CH_2$—;

- n being an integer ranging from 1 to 6 and m being an integer ranging from 1 to 10;
- $R_{10}$ represents a hydrogen atom, an alkoxy radical containing from 1 to 4 carbon atoms or a divalent radical —O— connected to the radical $R_9$ when the latter is also divalent;
- q represents an integer equal to 1 or 2, wherein if q is equal to 2, $R_9$ must represent a divalent radical; and
- Y and Y' each independently represents a hydrogen atom or an—$SO_3H$ radical, at least one of the radicals Y or Y' being other than hydrogen.

37. A composition according to claim 36, wherein, in formula (IV), q is equal to 1, Y and $R_{10}$ each represent a hydrogen atom, $R_9$ represents a methyl radical, and Y' in position 3 represents an —$SO_3H$ radical.

38. A composition according to claim 36, wherein, in formula (IV), q is equal to 1, Y represents an —$SO_3H$ radical, Y' represents a hydrogen atom and $R_{10}$ represents a divalent radical —O— connected to $R_9$ which represents a methylene radical.

39. A composition according to claim 36, wherein, in formula (IV), q is equal to 1, Y represents an —$SO_3H$ radical, Y' and $R_{10}$ both represent a hydrogen atom and $R_9$ represents a methyl radical.

40. A composition according to claim 36, wherein, in formula (IV), q is equal to 1, Y represents an —$SO_3H$ radical, Y' represents a hydrogen atom, $R_9$ represents a methyl radical and $R_{10}$ represents a methoxy radical.

41. A composition according to claim 36, wherein, in formula (IV), q is equal to 1, Y represents an —$SO_3H$ radical, Y' and $R_{10}$ both represent a hydrogen atom and $R_9$ represents an n-butyl radical.

42. A composition according to claim 36, wherein, in formula (IV), q is equal to 1, Y represents an —$SO_3H$ radical, Y' represents a hydrogen atom, $R_9$ represents an n-butyl radical and $R_{10}$ represents a methoxy radical.

43. A composition according to claim 22, wherein said compound which screens out UV radiation corresponds to formula (V) below:

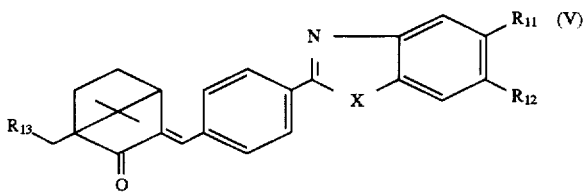

in which:

R₁₁ represents a hydrogen atom, a linear or branched alkyl or alkoxy radical containing from 1 to 6 carbon atoms or an —SO₃H radical;

R₁₂ represents a hydrogen atom or a linear or branched alkyl or alkoxy radical containing from 1 to 6 carbon atoms;

R₁₃ represents a hydrogen atom or an —SO₃H radical, at least one of the radicals R₁₁ and R₁₃ represents an —SO₃H radical; and X is an oxygen or sulphur atom or an —NR— group, R being a hydrogen atom or a linear or branched alkyl radical containing from 1 to 6 carbon atoms.

44. A composition according to claim 43, wherein, in formula (V), X represents an —NH— radical, R₁₁ represents an —SO₃H radical and R₁₂ and R₁₃ both represent a hydrogen atom.

45. A composition according to claim 22, wherein said compound which screens out UV radiation is a compound of formula (VI)

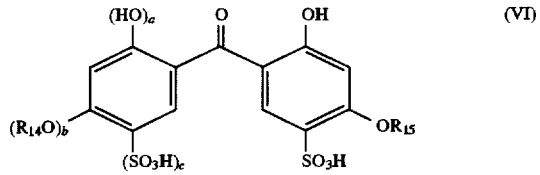

in which:

R₁₄ and R₁₅, which may be identical or different, represent a hydrogen atom or a linear or branched alkyl radical containing from 1 to 8 carbon atoms; and a, b and c, which may be identical or different, are equal to 0 or 1.

46. A composition according to claim 45, wherein, in formula (VI), a, b and c are equal to 0 and R₁₅ represents a methyl radical.

47. A composition according to claim 22, wherein said compound which screens out UV radiation is a compound of formula (VII)

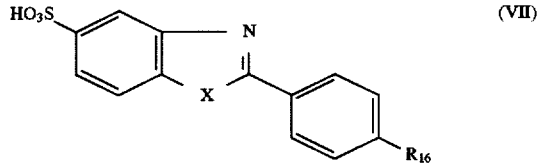

wherein:

X represents an oxygen atom or an —NH— radical;

R₁₆ represents a hydrogen atom, a linear or branched alkyl or alkoxy radical containing from 1 to 8 carbon atoms or a group of formula

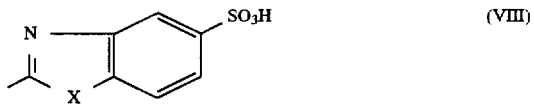

wherein X' represents an oxygen atom or an —NH— radical.

48. A composition according to claim 47, wherein, in formula (VII), X represents an —NH— radical and R₁₆ represents a hydrogen atom.

49. A composition according to claim 47, wherein, in formula (VII), X represents an —NH— radical and R₁₆ represents a group of formula (VIII) with X' representing an —NH— radical.

50. A composition according to claim 47, wherein, in formula (VII), X represents an oxygen atom and R₁₆ represents a group of formula (VIII) with X' representing an oxygen atom.

51. A composition according to claim 1, wherein said compound which screens out UV radiation is present in a concentration ranging from 0.1 to 10% by weight of active substance relative to the total weight of the composition.

52. A composition according to claim 51, wherein said compound, which screens out UV radiation is present in a concentration ranging from 0.5 to 5% by weight of active substance relative to the total weight of the composition.

53. A composition according to claim 1, which further comprises an oil dispersed in said lipid vesicles and optionally comprises at least one liposoluble cosmetic or dermatological active agent present in said oil.

54. A composition according to claim 1, which further comprises, in said aqueous phase, at least one water-soluble cosmetic or dermatological active agent.

55. A composition according to claim 1, which further comprises at least one adjuvant selected from gelling agents, preserving agents, dyes, opacifiers and fragrances.

56. A composition for topical use, which comprises a composition according to claim 1.

57. A method for treating or caring for the skin, the scalp, the hair, the eyelashes, or the eyebrows, which comprises applying to said skin, scalp, hair, eyelashes or eyebrows an effective amount of a treatment or care product which contains a composition according to claim 1 as a base.

58. A method for preparing a make-up product which comprises including a composition according to claim 1 as a base for said make-up product.

59. A method for the non-therapeutic protection of the hair, scalp, the eyelashes or the eyebrows against ultraviolet rays, which comprises applying an effective amount of a cosmetic composition to said skin, hair, scalp, eyelashes or eyebrows, wherein said cosmetic composition contains a composition according to claim 1 as a base.

* * * * *

UNITED STATES PATENT AND TRADEMARK OFFICE
CERTIFICATE OF CORRECTION

PATENT NO. : 5,759,526
DATED : June 2, 1998
INVENTOR(S) : Jean-Thierry SIMONNET et al.

It is certified that error appears in the above-identified patent and that said Letters Patent is hereby corrected as shown below:

Title page, item [54], title line 5, "USESS" should read --USES--.

Claim 24, column 16, line 49, "-Z" should read --Z--.

Claim 27, column 17, line 17, "form" should read --formula--.

Claim 31, column 17, line 28, "an-SO3H" should read --an -SO3H--.

Signed and Sealed this

Twenty-fifth Day of August, 1998

Attest:

BRUCE LEHMAN

*Attesting Officer*  *Commissioner of Patents and Trademarks*